United States Patent
Dieckmann et al.

(10) Patent No.: US 7,378,239 B2
(45) Date of Patent: May 27, 2008

(54) METHOD OF DIFFERENTIATING BETWEEN ULCERATIVE COLITIS AND CROHN'S DISEASE

(75) Inventors: Andreas Dieckmann, Bromma (SE); Robert Lofberg, Djursholm (SE); Oliver Von Stein, Spanga (SE); Petra Von Stein, Spanga (SE)

(73) Assignee: InDex Diagnostics AB, Stockholm (SE)

( * ) Notice: Subject to any disclaimer, the term of this patent is extended or adjusted under 35 U.S.C. 154(b) by 334 days.

(21) Appl. No.: 10/469,587

(22) PCT Filed: Jun. 25, 2003

(86) PCT No.: PCT/SE03/01105

§ 371 (c)(1),
(2), (4) Date: Jul. 16, 2004

(87) PCT Pub. No.: WO04/001073

PCT Pub. Date: Dec. 31, 2003

(65) Prior Publication Data

US 2004/0241823 A1    Dec. 2, 2004

Related U.S. Application Data

(60) Provisional application No. 60/409,213, filed on Sep. 10, 2002, provisional application No. 60/407,713, filed on Sep. 4, 2002, provisional application No. 60/407,682, filed on Sep. 4, 2002, provisional application No. 60/395,631, filed on Jul. 15, 2002, provisional application No. 60/395,629, filed on Jul. 15, 2002.

(30) Foreign Application Priority Data

| Jun. 25, 2002 | (SE) | 0201954-5 |
| Jun. 25, 2002 | (SE) | 0201956-0 |
| Jul. 18, 2002 | (SE) | 0202251-5 |
| Jul. 18, 2002 | (SE) | 0202252-3 |
| Jul. 18, 2002 | (SE) | 0202256-4 |

(51) Int. Cl.
*C12Q 1/68* (2006.01)
*C07H 21/04* (2006.01)

(52) U.S. Cl. ............... 435/6; 536/23.1; 536/23.5; 536/24.31

(58) Field of Classification Search ............... None
See application file for complete search history.

(56) References Cited

U.S. PATENT DOCUMENTS

2003/0158254 A1*  8/2003  Zerangue et al. ........... 514/484

OTHER PUBLICATIONS

Lawrence et al. Ulcerative colitis and Crohn's disease: distinctive gene expression profiles and novel susceptibility candidte genes. Human Molecular Genetics, vol. 10, No. 5, pp. 445-456, 2001.*
Online Mendelian Inheritance in Man, OMIM (TM). Johns Hopkins University, Baltimore, MD. MIM No.: 607178: Nov. 22, 2002: , World Wide Web URL: http://www.ncbi.nlm.nih.gov/omim/.*
Anderle et al. Changes in the transcriptional profile of transporters in the intestine along the anterior-posterior and crypt-villus axes. BMC Genomics, vol. 6, No. 1, p. 69 (pp. 1/17-17-17), May 2005.*
GenBank Accession No. XM_010112.1, GI: 11419739, publicly available Nov. 2000.*
Haila et al. SLC26A2 (diastrophic dysplasia sulfate transporter) is expressed in developing and mature cartilage but also in other tissues and cell types. The Journal of Histochemistry & Cytochemistry, vol. 49, No. 8, pp. 973-982, Aug. 2001.*
Hastbacka et al. Identification of the Finnish founder mutation for diastrophic dysplasia (DTD). European Journal of Human Genetics, vol. 7, No. 6, pp. 664-670, Sep. 1999.*
Buck et al. Design strategies and performance of custom DNA sequencing primers. Biotechniques, vol. 27, No. 3, pp. 528-536, Sep. 1999.*
A. Imada et al., "Coordinate Upregulation of Interleukin-8 and Growth-Related Gene Product-60 is Present in the Colonic Mucosa of Inflammatory Bowel Disease," Scand. J. Gastroenterol., V. 36, 2001, pp. 854-864.
Ken J. Newell et al., "Matrilysin (Matrix Metalloproteinase-7) Expression in Ulcerative Colitis-Related Tumorigenesis," Molecular Carcinogenesis, V. 34, 2002, pp. 59-63.
Kim L. Isaacs et al., "Cytokine Messenger RNA Profiles in Inflammatory Bowel Disease Mucosa Detected by Polymerase Chain Reaction Amplification," Gastroenterology, V. 103, 1992, pp. 1587-1595.
J.C. Hartupee et al., "Isolation and Characterization of a cDNA Encoding a Novel Member of the Human Regenerating Protein Family: Reg IV[1]," Biochimica et Biophysica Acta, V. 1518, 2001, pp. 287-293.
Keiki Matsuno et al., "The Expression of Matrix Metalloproteinase Matrilysin Indicates the Degree of Inflammation in Ulcerative Colitis," Journal of Gastroenterology, V. 38, 2003, pp. 348-354.

* cited by examiner

*Primary Examiner*—Daniel M. Sullivan
*Assistant Examiner*—Jennifer Dunston
(74) *Attorney, Agent, or Firm*—DLA Piper US LLP

(57) ABSTRACT

The differentiation between ulcerative colitis and Crohn's disease is made possible by a multi-gene approach where gene expression profiles in biopsy samples obtained from inflamed, and optionally also non-inflamed, areas in the intestines of a patient are studied.

13 Claims, 1 Drawing Sheet

SEQUENCE LISTING

<160> NUMBER OF SEQ ID NOS: 26

<210> SEQ ID NO 1
<211> LENGTH: 4520
<212> TYPE: DNA
<213> ORGANISM: Homo sapiens

<400> SEQUENCE: 1

```
taggaacagg ggagagtgca cctgctacca gtcaagctca gccagactgc aagaggaggc      60
gaggcggagc cagccgaggg agtgaaccat ggacaagttg aaatgcccga gtttcttcaa     120
gtgcaggagg aaggagaaag tgtcggcttc atcagagaat ttccatgttg gtgaaaatga     180
tgagaatcag gaccgtggta actggtccaa aaaatcggat tatcttctat ctatgattgg     240
atacgcagtg ggattaggaa atgtgtggag atttccatat ctgacctaca gcaatggtgg     300
aggcgccttc ttgatacctt atgcaattat gttagcattg gctggtttac ctttgttctt     360
tctggagtgt tcactgggac aatttgctag cttaggtcca gtttcagttt ggaggattct     420
tccattgttt caaggtgtgg gaattacaat ggtcctgatc tccattttg tgacaatcta      480 ttacaatgtc ataattgcct atagtcttta ctacatgttt gcttcttttc aaagtgaact     540
accatggaaa aattgttctt cgtggtcaga taaaaactgt agcagatcac caatagtaac     600
tcactgtaat gtgagtacag tgaataaagg aatacaagag atcatccaaa tgaataaaag     660
```

```
ctgggtagac atcaacaatt ttacctgcat caacggcagt gaaatttatc agccagggca    720
gcttcccagt gaacaatatt ggaataaagt ggcgctccaa cggtcaagtg aatgaatga     780
gactggagta attgtttggt atttagcact ttgtcttctt ctggcttggc tcatagttgg    840
agcagcacta tttaaaggaa tcaaatcgtc tggcaaggtg gtatatttta cagctctttt    900
cccctatgtg gtcctactca tcctgttagt acgaggtgca actctggagg gtgcttcaaa    960
aggcatttca tactatattg gagcccagtc aaattttaca aaacttaagg aagctgaggt   1020
atggaaagat gctgccactc agatatttta ctccctttca gtggcttggg gtggcttagt   1080
tgctctatca tcttacaata agttcaaaaa caactgcttc tctgatgcca ttgtggtttg   1140
tttgacaaac tgtctcacta gcgtgtttgc tggattgct atttttttcta tattgggaca   1200
catggcccat atatctggaa aggaagtttc tcaagttgta aaatcaggtt ttgatttggc   1260
attcattgcc tatccagagg ctctagccca actcccaggt ggtccatttt ggtccatatt   1320
atttttttc atgcttttaa ctttgggtct cgattctcag tttgcttcga ttgaaacgat   1380
cacaacaaca attcaagatt tatttcccaa agtgatgaag aaaatgaggg ttcccataac   1440
tttgggctgc tgcttggttt tgtttctcct tggtctcgtc tgtgtgactc aggctggaat   1500
ttactgggtt catctgattg accacttctg tgctggatgg ggcattttaa ttgcagctat   1560
actggagcta gttggaatca tctggattta tggagggaac agattcattg aggatacaga   1620
aatgatgatt ggagcaaaga ggtggatatt ctggctatgg tggagagctt gctggttttgt  1680
aattacgcct atcctttga ttgcaatatt tatctggtca ttggtgcaat tcatagacc    1740
taattatggc gcaattccat accctgactg gggagttgct ttaggctggt gtatgattgt   1800
tttctgcatt atttggatac caattatggc tatcataaaa ataattcagg ctaaaggaaa   1860
catctttcaa cgccttataa gttgctgcag accagcttct aactgggtc catacctgga   1920
acaacatcgt ggggaaagat ataaagacat ggtagatcct aaaaaagagg ctgaccatga   1980
aatacctact gttagtggca gcagaaaacc ggaatgagat ctcattgaaa aaaatatatg   2040
attgtataat gtgatttttt ttagaatagg gggaaccta tttatttgtg tgttaactga   2100
ataggaaaat gtacatacta tgttcatgat agtgtgattt ttttcacatt taagcaggaa   2160
tgcaatataa aaatgtgaat ctcttaattc tcagccatgt gcttattata tttcttttta   2220
gattgtctat ctgtataaca cacacacaca cacctaagag tctctatttc acaattatat   2280
ttttgtaaat agtatatgca ttttaatac attggaggct ttattttgaa ctaatttctt    2340
agagaatagt tatattttct attacacaag tttaaaaata ttattaactt gtattttctt   2400
aatatacaat ctatcttttc cacaaatatg agtgggaaat aaatcagcac atttgaaaga   2460
aagtgttaaa actgaaggcc tcacttaatt agaaacgtga taaatatatg gacaaatgga   2520
ctatacatac tataagagga ctgtagttta atactttta cccaaatatg tttaaaaaca   2580
tcgtgcattt gttacagctc atgttttcta tatgaactta gtcattaatg ttctttataa   2640
aaagtgaaat aagatggaaa aattaggatc ctacagccag tacgtgataa atctagaaaa   2700
ttgagttttg agtacctctt tttcccatata caatcttcct tccttaggta atttggaaga   2760
aaactatgac ccatttaatt tctattgtgt ttcaccaaat tcagtgttgt tcattatacc   2820
tctctgaaat ataggtttaa tttcaaatag aatatggact taaatgttaa tgagaaactg   2880
gctttaatca attctagcat tttattactg taatacaggg ctgatagagt gattttgtct   2940
tatatgagtc agttactact tacaggtgat aacttgcata ctattggaag ataaagttgt   3000
```

```
caaacttgtc aagaatgaga aaagccaaat tagaaaatcc tatgtcctag tttccttacc    3060
aaggataatt aaatatatca ctaagagctt tatatattga ttatatattg ttgacaactg    3120
gtttaagcat catagcctat gatgataaac actgcctata tatgtaaata gcttttcatc    3180
aattcttaaa tttcttaacc taggcttcag ggagcatatg aaaccaaaat tatatggaac    3240
attttctgtg tgtacatgta catgcatttt tctagggaga gagtccgtag gtttatcaga    3300
atatcaagga aaactgtgac ccaaagaagt ttaagaatca catacagtgc tgctggcttt    3360
ttgtgcttgg caaatgagtg acaatagaag aaataatttt tcttacacat tttaaaacgt    3420
tttctcttcc ttgtgattga agatgaaagg agtaagaaat taaggcattt gtttaattta    3480
tactggtaac ttatttaggg gggaggggac atgaaggtag gtaaataggt aggcctctaa    3540
ttgaaccacc tctctaagtt atgtacgtat atataagctg aaattgtgtt tgacattctg    3600
agggttttct ttttcttttt ccttttttttt ttttttggt gggggctgg gggtcagagt    3660
cttgttctgt tgcctgggct ggagtgcagt ggcatgatct cagctcactg caacctctgc    3720
cttctggatt caagtgattc tcctgcctca gcctcttgag tagctgggac tacaggtgcc    3780
cgccaccaca ccagctaatt tttgtatttt tagtagaggc gaagtttccc catgttggcc    3840
aggctggtct tgaactcccg acctcaagtg atctgtctac ctcggcctcc taaagtgctg    3900
agattacagg tgtgagccac cgtgcccggc ccattctaag ggttttcttt gaagacaggt    3960
caaatgctgt tagtaagttt caggagattg ttaattcctc agttatacca gatttttataa   4020
aatatttgag aatagatggc taacaagagg ttagaaatac ttttccttaa ttttaatcca    4080
cagtatgtta catgcattct accactacat tttggtgcta tttaaggtgt gcaattttct    4140
ataggtgact tttgcaattc agggaagatt tgggcatatt aaatgaaaga atatctaatt    4200
gggggaggtg tgaagggaaa gaaattcttt tcaaagctg accacaaaga gtagttaaaa    4260
gttttttgtca ctatcttcac aagtgtgtaa agcacagatt tcaacagagt gcttggcata    4320
ttgtagggtg ctcaatggtg gttttttatta ttattactca gattccacag tggcaagaaa    4380
catcattcta cataatggaa aacatttaca tcaaatccca cttactttaa tgcgaacttg    4440
gagataattt atggtattgt attgtaaacc attaatgaaa acttttttcac agttgagtga    4500
aattaaaatc actatatctc                                                4520
```

<210> SEQ ID NO 2
<211> LENGTH: 2832
<212> TYPE: DNA
<213> ORGANISM: Homo sapiens

<400> SEQUENCE: 2

```
aggaagctga accatctatc tccagaaatg tcttcagaaa gtaaagagca acataacgtt      60
tcacccagag actcagctga aggaaatgac agttatccat ctgggatcca tctggaactt     120
caaagggaat caagtactga cttcaagcaa tttgagacca atgatcaatg cagaccttat     180
cataggatcc ttattgagcg tcaagagaaa tcagatacaa acttcaagga gtttgttatt     240
aaaaagctgc agaagaattg ccagtgcagt ccagccaaag ccaaaaatat gattttaggt     300
ttccttcctg tttttgcagtg gctcccaaaa tacgacctaa agaaaaacat tttaggggat     360
gtgatgtcag gcttgattgt gggcatatta ttggtgcccc agtccattgc ttattccctg     420
ctggctggcc aagaacctgt ctatggtctg tacacatctt ttttgccag catcatttat     480
tttctcttgg gtacctcccg tcacatctct gtgggcattt ttgagtgact gtgccttatg     540
attggtgaga cagttgaccg agaactacag aaagctggct atgacaatgc ccatagtgct     600
```

```
ccttccttag gaatggtttc aaatgggagc acattattaa atcatacatc agacaggata      660
tgtgacaaaa gttgctatgc aattatggtt ggcagcactg taacctttat agctggagtt      720
tatcaggtag cgatgggctt ctttcaagtg ggttttgttt ctgtctacct ctcagatgcc      780
ttgctgagtg gatttgtcac tggtgcctcc ttcactattc ttacatctca ggccaagtat      840
cttcttgggc tcaaccttcc tcggactaat ggtgtgggct cactcatcac tacctggata      900
catgtcttca gaaacatcca taagaccaat ctctgtgatc ttatcaccag ccttttgtgc      960
cttttggttc ttttgccaac caaagaactc aatgaacact tcaaatccaa gcttaaggca     1020
ccgattccta ttgaacttgt tgttgttgta gcagccacat tagcctctca ttttggaaaa     1080
ctacatgaaa attataattc tagtattgct ggacatattc ccactgggtt tatgccaccc     1140
aaagtaccag aatggaacct aattcctagt gtggctgtag atgcaatagc tatttccatc     1200
attggttttg ctatcactgt atcactttct gagatgtttg ccaagaaaca tggttacaca     1260
gtcaaagcaa accaggaaat gtatgccatt ggcttttgta atatcatccc ttccttcttc     1320
cactgtttta ctactagtgc agctcttgca aagacattgg ttaaagaatc aacaggctgc     1380
catactcagc tttctggtgt ggtaacagcc ctggttcttt tgttggtcct cctagtaata     1440
gctcctttgt tctattccct tcaaaaaagt gtccttggtg tgatcacaat tgtaaatcta     1500
cggggagccc ttcgtaaatt tagggatctt cccaaaatgt ggagtattag tagaatggat     1560
acagttatct ggtttgttac tatgctgtcc tctgcactgc taagtactga ataggccta     1620 cttgttgggg tttgttttc tatattttgt gtcatcctcc gcactcagaa gccaaagagt     1680
tcactgcttg gcttggtgga agagtctgag gtctttgaat ctgtgtctgc ttacaagaac     1740
cttcagacta agccaggcat caagattttc cgctttgtag cccctctcta ctacataaac     1800
aaagaatgct ttaaatctgc tttatacaaa caaactgtca acccaatctt aataaaggtg     1860
gcttggaaga aggcagcaaa gagaaagatc aaagaaaaag tagtgactct tggtggaatc     1920
caggatgaaa tgtcagtgca actttcccat gatcccttgg agctgcatac tatagtgatt     1980
gactgcagtg caattcaatt tttagataca gcagggatcc acacactgaa agaagttcgc     2040
agagattatg aagccattgg aatccaggtt ctgctggctc agtgcaatcc cactgtgagg     2100
gattccctaa ccaacggaga atattgcaaa aaggaagaag aaaaccttct cttctatagt     2160
gtgtatgaag cgatggcttt tgcagaagta tctaaaaatc agaaaggagt atgtgttccc     2220
aatggtctga gtcttagtag tgattaattg agaaggtaga tagaagaatg tctagccaat     2280
aggttaaaat ttcaagtgtc caacattcc cagttccaca gtgggaaatt ttgcacactt     2340 gaaatttaa ccaagtggct agatattatt cctcctttga agctaatggc atttgtatat     2400
acacactgca gcagagcttg tagctggaca gagtcaaaaa gaagaaaata cggtttcagg     2460
ctttcttgca gatatgaagt attcttggaa tgcaataagt atgtattgaa ctgtactgta     2520
aagtagctcc aaaacttaat tactctcctg ttttaggggt tatacatttg gactgtgcat     2580
tctccaagag atgaagcggt gaagttggga tttacattgg aagtgctgta gacttcttta     2640
tgtggctcag tggagagagg gaaagaatgt tgcacctgct ctagtaccat aggtcaagag     2700
gcttctggat cacaaagtca taactagaca ggtttgttct tgtagttttc tatcccagt     2760 ctttgctccc cagatggcag tagtttttag taggaaagtg ccattcctgt ccttaaggca     2820
cagtctcatc ag                                                         2832
```

<210> SEQ ID NO 3

```
<211> LENGTH: 1103
<212> TYPE: DNA
<213> ORGANISM: Homo sapiens

<400> SEQUENCE: 3
cacagagccc gggccgcagg cacctcctcg ccagctcttc cgctcctctc acagccgcca      60
gacccgcctg ctgagcccca tggcccgcgc tgctctctcc gccgccccca gcaatccccg     120
gctcctgcga gtggcactgc tgctcctgct cctggtagcc gctggccggc cgcagcagg     180
agcgtccgtg ccactgaac tgcgctgcca gtgcttgcag accctgcagg gaattcaccc     240
caagaacatc caaagtgtga acgtgaagtc ccccggaccc cactgcgccc aaaccgaagt     300
catagccaca ctcaagaatg gcggaaaagc ttgcctcaat cctgcatccc ccatagttaa     360
gaaaatcatc gaaaagatgc tgaacagtga caaatccaac tgaccagaag ggaggaggaa     420
gctcactggt ggctgttcct gaaggaggcc ctgcccttat aggaacagaa gaggaaagag     480
agacacagct gcagaggcca cctggattgt gcctaatgtg tttgagcatc gcttaggaga     540
agtcttctat ttatttattt attcattagt tttgaagatt ctatgttaat attttaggtg     600
taaaataatt aagggtatga ttaactctac ctgcacactg tcctattata ttcattcttt     660
ttgaaatgtc aaccccaagt tagttcaatc tggattcata tttaatttga aggtagaatg     720
ttttcaaatg ttctccagtc attatgttaa tatttctgag gagcctgcaa catgccagcc     780
actgtgatag aggctggcgg atccaagcaa atggccaatg agatcattgt gaaggcaggg     840
gaatgtatgt gcacatctgt tttgtaactg tttagatgaa tgtcagttgt tatttattga     900
aatgatttca cagtgtgtgg tcaacatttc tcatgttgaa actttaagaa ctaaaatgtt     960
ctaaatatcc cttggacatt ttatgtcttt cttgtaaggc atactgcctt gtttaatggt    1020
agttttacag tgtttctggc ttagaacaaa ggggcttaat tattgatgtt tcatagaga     1080
atataaaaat aaagcactta tag                                            1103

<210> SEQ ID NO 4
<211> LENGTH: 1140
<212> TYPE: DNA
<213> ORGANISM: Homo sapiens

<400> SEQUENCE: 4
ggcacgaggg tccaagaaca attgtctctg gacggcagct atgcgactca ccgtgctgtg      60
tgctgtgtgc ctgctgcctg gcagcctggc cctgccgctg cctcaggagg cgggaggcat     120
gagtgagcta cagtgggaac aggctcagga ctatctcaag agattttatc tctatgactc     180
agaaacaaaa aatgccaaca gtttagaagc caaactcaag gagatgcaaa aattctttgg     240
cctacctata actggaatgt taaactccca cgtcatagaa ataatgcaga gcccagatg     300
tggagtgcca gatgttgcag aatactcact atttccaaat agcccaaaat ggacttccaa     360
agtggtcacc tacaggatcg tatcatatac tcgagactta ccgcatatta cagtggatcg     420
attagtgtca aaggctttaa acatgtgggg caaagagatc cccctgcatt tcaggaaagt     480
tgtatgggga actgctgaca tcatgattgg ctttgcgcga ggagctcatg ggactcccta     540
cccatttgat gggccaggaa acacgctggc tcatgccttt gcgcctggga caggtctcgg     600
aggagatgct cacttcgatg aggatgaacg ctggacggat ggtagcagtc tagggattaa     660
cttcctgtat gctgcaactc atgaacttgg ccattctttg ggtatgggac attcctctga     720
tcctaatgca gtgatgtatc caacctatgg aaatggagat ccccaaaatt ttaaactttc     780
ccaggatgat attaaaggca ttcagaaact atatggaaag agaagtaatt caagaaagaa     840
```

```
atagaaactt caggcagaac atccattcat tcattcattg gattgtatat cattgttgca      900
caatcagaat tgataagcac tgttcttcca ctccatttag caattatgtc acccttttt       960 attgcagttg gttttgaat gtctttcact ccttttaagg ataaactcct ttatggtgtg      1020
actgtgtctt attcatctat acttgcagtg ggtagatgtc aataaatgtt acatacacaa     1080
ataaataaaa tgtttattcc atggtaaatt taaaaaaaaa aaaaaaaaaa aaaaaaaaa      1140

<210> SEQ ID NO 5
<211> LENGTH: 345
<212> TYPE: DNA
<213> ORGANISM: Homo sapiens

<400> SEQUENCE: 5
atgtcggccc tcagcctcct cattctgggc ctgctcacgg cagtgccacc tgccagctgt       60
cagcaaggcc tggggaacct tcagccctgg atgcagggcc ttatcgcggt ggccgtgttc      120
ctggtcctcg ttgcaatcgc ctttgcagtc aaccacttct ggtgccagga ggagccggag      180
cctgcacaca tgatcctgac cgtcggaaac aaggcagatg gagtcctggt gggaacagat      240
ggaaggtact cttcgatggc ggccagtttc aggtccagtg agcatgagaa tgcctatgag      300
aatgtgcccg aggaggaagg caaggtccgc agcaccccga tgtaa                      345

<210> SEQ ID NO 6
<211> LENGTH: 1180
<212> TYPE: DNA
<213> ORGANISM: Homo sapiens

<400> SEQUENCE: 6
cactgaagaa ggcagggggcc ttagagtct tggttgccaa acagatttgc agatcaagga      60
gaacccagga gtttcaaaga agcgctagta aggtctctga tccttgca ctagctacat       120 cctcagggta ggaggaagat ggcttccaga agcatgcggc tgctcctatt gctgagctgc     180
ctggccaaaa caggagtcct gggtgatatc atcatgagac ccagctgtgc tcctggatgg     240
ttttaccaca agtccaattg ctatggttac ttcaggaagc tgaggaactg gtctgatgcc     300
gagctcgagt gtcagtctta cggaaacgga gcccacctgg catctatcct gagtttaaag     360
gaagccagca ccatagcaga gtacataagt ggctatcaga aagccagcc gatatggatt      420 ggcctgcacg acccacagaa gaggcagcag tggcagtgga ttgatggggc catgtatctg     480
tacagatcct ggtctggcaa gtccatgggt gggaacaagc actgtgctga gatgagctcc     540
aataacaact ttttaacttg gagcagcaac gaatgcaaca gcgccaaca cttcctgtgc     600 aagtaccgac catagagcaa gaatcaagat tctgctaact cctgcacagc cccgtcctct     660
tcctttctgc tagcctggct aaatctgctc attatttcag aggggaaacc tagcaaacta     720
agagtgataa gggccctact acactggctt ttttaggctt agagacagaa actttagcat     780
tggcccagta gtggcttcta gctctaaatg tttgccccgc catcccttc cacagtatcc      840 ttcttccctc ctccctgtc tctggctgtc tcgagcagtc tagaagagtg catctccagc     900
ctatgaaaca gctgggtctt tggccataag aagtaaagat ttgaagacag aaggaagaaa     960
ctcaggagta agcttctagc ccccttcagc ttctacaccc ttctgccctc tctccattgc    1020
ctgcacccca cccagccac tcaactcctg cttgttttc ctttggccat gggaaggttt      1080
accagtagaa tccttgctag gttgatgtgg gccatacatt cctttaataa accattgtgt     1140
acataaaaaa aaaaaaaaaa aaaaaaaaa aaaaaaaaa                            1180
```

<210> SEQ ID NO 7
<211> LENGTH: 3109
<212> TYPE: DNA
<213> ORGANISM: Homo sapiens

<400> SEQUENCE: 7

```
cattggactt cagcatgact actcagttgc cagcttacgt ggcaattttg ctttctatg       60
tctcaagagc cagctgccag gacactttca ttgcagctgt ttatgagcat gcagcgatat     120
tgcccaatgc caccctaaca ccagtgtctc gtgaggaggc tttggcatta atgaatcgga     180
atctggacat tttggaagga gcgatcacat cagcagcaga tcagggtgcg catattattg     240
tgactccaga agatgctatt tatggctgga acttcaacag ggactctctc tacccatatt     300
tggaggacat cccagaccct gaagtaaact ggatcccctg taataatcgt aacagatttg     360
gccagacccc agtacaagaa agactcagct gcctggccaa gaacaactct atctatgttg     420
tggcaaatat tggggacaag aagccatgcg ataccagtga tcctcagtgt ccccctgatg     480
gccgttacca atacaacact gatgtggtat tgattctca aggaaaactg gtggcacgct      540
accataagca aaaccttttc atgggtgaaa atcaattcaa tgtacccaag agcctgaga     600
ttgtgacttt caataccacc tttggaagtt ttggcatttt cacatgcttt gatatactct     660
tccatgatcc tgctgttacc ttggtgaaag atttccacgt ggacaccata gtattcccaa     720
cagcttggat gaatgttttg ccacatttgt cagctgttga attccactca gcttgggcta     780
tgggcatgag ggtcaatttc cttgcatcca acatacatta cccctcaaag aaaatgacag     840
gaagtggcat ctatgcaccc aattcttcaa gagcatttca ttatgatatg aagacagaag     900
agggaaaact cctcctctcg caactggatt cccacccatc ccattctgca gtggtgaact     960
ggacttccta tgccagcagt atagaagcgc tctcatcagg aaacaaggaa tttaaaggca    1020
ctgtcttttt cgatgaattc acttttgtga agctcacagg agttgcagga aattatacag    1080
tttgtcagaa agatctctgc tgtcatttaa gctacaaaat gtctgagaac ataccaaatg    1140
aagtgtacgc tctaggggca tttgacggac tgcacactgt ggaagggcgc tattatctac    1200
agatttgtac cctgttgaaa tgtaaaacga ctaatttaaa cacttgcggt gactcagctg    1260
aaacagcttc taccaggttt gaaatgttct ccctcagtgg cactttcgga acccagtatg    1320
tcttttcctga ggtgttgctg agtgaaaatc agcttgcacc tggagaattt caggtgtcaa    1380
ctgacgacg cttgttttagt ctgaagccaa catccggacc tgtcttaaca gtaactctgt    1440
ttgggaggtt gtatgagaag gactgggcat caaatgcttc atcaggcctc acagcacaag    1500
caagaataat aatgctaata gttatagcac ctattgtatg ctcattaagt tggtagaata    1560
ttgactttt ctcttttta tttgggataa tttaaaaaat gatggatgag aaaagaaaga    1620
ttggtccggg ttaatattat cctctagtat aagtgaatta ctagtttctc tttatttaga    1680
caaacacaca cacaccagat aatataaact taataaatta tctgttaatg tagattttat    1740
ttaaaaaact atatttgaac attggtcttt cttggacgtg agctaattat atcaaataag    1800
tatcacaaat cttttacgca gaagaaataa aaactacggg tagaaaacat aagaactatc    1860
ataaaattta cttacaagga ggctgctctt gttaccactt ttattatatt acgtatcact    1920
tattcagctc tgctgaaaat ttccaatgac tttgtttgtt tgctctttta gttttttacc    1980
taaacaatac attttgattc tcttgtgggt tgataatgtc tccccaaaat ttacatgttg    2040
aagcacctca gaatgtgact gtatttggag acagggtctt taagaggta aaataaggtc    2100
attaggatag acccctaattc aatatgactg atgatcataa agaagaggc gagtagggca    2160
```

-continued

```
caacaggcac aaagggagac cataaggaga cacagaggaa ggacaactct ttacaagcta    2220
agaagagagg gcctcagaag aaaccaaccc tgccaacacc ttgatcttgg acttccagcc    2280
tccaaaacta tgagaaataa atttctattg tttaagtcac ccagtccatg gtactttgtt    2340
aggcagccct ggcaaatgaa tcaaagaccc attcctgttc ctctccccac cactactgtt    2400
ttctactgta atctgaagct tcaacaaaag gcttacctgg taagaatatt cagctggtct    2460
gggtcctcaa gactccaata gacactctta agaaggatt gctgatggat tgatagtgaa     2520
accattagat cattgaattc ctctggaatt agaaaaccag agagtcccat ttaagaaat     2580 tagatattta atatagcatt gtgtgttcta ttttagtaac agcagaatct cttgacatta    2640
cacaactcag tgaaacaaca tcatttaagc caaaatatct cccaactgac tgatagactc    2700
tgagcactaa tatcatagtg ctgtgatgat ggacaattac atagtaccga taacagccat    2760
gcactgtgca aagcatgccc ttctgcacag gagagcaagg cacttgcagt agtgatctat    2820
gccagcaaaa catcattttg agacaaacat ttttgtggca gatgttttc ctaaaaagta     2880 ctatatcatc caagaaatat ttgagtaaaa tcccttgttc ttttgggtga cattaactga    2940
catttgcttt ttttcaagac ctaatagaaa ataagaaagc ccataatgta tttagaaaca    3000
ggaatcctca gagcaattct ctgtattctc ataatttc aatgtaaaac agaaaacata      3060
ttgatgtgtt ggtgataggc ttgaattatt aaaaacttca aaaacaaaa                3109
```

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
tagtctatga tcgtcgacgg ctgatgaagc ggccgctgga gttttttttt ttttttttv    60
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
tgatgaagcg gccgctgg                                                  18
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
ttcatcagcc gtcgacgatc                                                20
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
cgtaagcttg gatcctctag agc                                          23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgcaggtacc ggtccggaat tcc                                          23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgctgagat tacaggtgtg agcc                                         24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccttcacac ctcccccaat taga                                         24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtggagagag ggaaagaatg ttgc                                         24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccagtttagg acagattcca tggg                                         24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 17
gtgcctaatg tgtttgagca tcgc                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcccctttgt tctaagccag aaac                                              24

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caggcagaac atccattcat tcattc                                            26

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gacatctacc cactgcaagt atag                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccgtcggaaa caaggcagat ggag                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaaggacgtg tgagcaggat ggga                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 23
ggtgggaaca agcactgtgc tgag                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggctggagat gcactcttct agac                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gccagcaaaa catcattttg agac                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcctatcacc aacacatcaa tatg                                              24
```

METHOD OF DIFFERENTIATING BETWEEN ULCERATIVE COLITIS AND CROHN'S DISEASE

CROSS REFERENCE TO RELATED APPLICATIONS

This application is a 35 USC § 371 National Stage application of application No. PCT/SE2003/001105 filed Jun. 25, 2003; which claims the benefit under 35 USC §119(e) to U.S. application Ser. No. 60/409,213 filed Sep. 10, 2002, now abandoned; U.S. application Ser. No. 60/407,713 filed Sep. 4, 2002, now abandoned; U.S. application Ser. No. 60/407,682 filed Sep. 4, 2002, now abandoned; U.S. application Ser. No. 60/395,631 filed Jul. 15, 2002, now abandoned and U.S. application Ser. No. 60/395,629 filed Jul. 15, 2002, now abandoned. PCT Application No. PCT/SE2003/001105 filed Jun. 25, 2003 also claims the benefit under 35 USC §119(a) to Sweden Application No. 0201954-5 filed Jun. 25, 2002; Sweden Application No. 0201956-0 filed Jun. 25, 2002; Sweden Application No. 0202251-5 filed Jul. 18, 2002; Sweden Application No. 0202251-5 filed Jul. 18, 2002; Sweden Application No. 0202252-3 filed Jul. 18, 2002. The disclosure of each of the prior applications is considered part of and is incorporated by reference in the disclosure of this application.

FIELD OF THE INVENTION

The present invention relates the diagnosis of inflammatory bowel diseases, and in particular to a method and kit for the prediction and/or diagnosis of ulcerative colitis. The invention discloses specific marker genes whose change in expression status, either collectively or a sub-set thereof, is indicative of ulcerative colitis. The present invention further relates to DNA-related methods by which quantification of the expression levels of said disease-associated marker genes directly from a biopsy allows for an immediate and accurate diagnostic test for disease type, and/or the assessment of the effect of a particular treatment regimen. The invention further discloses diagnostic kits for the detection of the expressions levels of said genes.

BACKGROUND OF THE INVENTION

Inflammatory bowel disease (IBD) is a term encompassing several conditions involving chronic inflammation in the gastrointestinal tract. Two of the most debilitating forms of IBD are ulcerative colitis (UC) and Crohn's disease (CD). These diseases affect young people, with a typical debut at the age of 20-30 years, and disease management is a long-term commitment for both patient and physician, since there is currently no cure for either condition. Approximately 30% of IBD patients undergo surgery during their lifetime and patients with long-standing IBD are at considerable risk of developing colorectal cancer. Three out of ten IBD patients do not respond to the best available medical therapy today, even when high doses are used, causing considerable side effects.

Treatment of patients with active UC aims at reducing inflammation and promoting colon healing and mucosal recovery. The underlying cause of UC is not understood, nor is it known what triggers the disease to recur between its inactive and active forms. However, the active stage of the disease is characterised by significant inflammation of the mucosa, increased cell permeability, loss of protein and fluids. In severe stages deep inflammation of the bowel wall may develop with abdominal tenderness, tachycardia, fever and risk of bowel perforation.

One early symptom of ulcerative colitis is constipation with passage of blood or mucus in the stools. Several months or years may pass before diarrhoea develops with abdominal pain. Later symptoms include severe fatigue, weight loss, loss of appetite, fever and occasionally arthralgia.

The road to an established diagnosis of ulcerative colitis often includes a thorough study of the patient's medical history, the exclusion of other conditions, as well as several tests, e.g. blood tests, stool examination, barium enema X-ray, sigmoidoscopy, colonoscopy, and biopsy. The biopsy may be performed as part of a sigmoidoscopy or colonoscopy examination.

It is obvious that a possibility to clinically distinguish UC from colonic CD at an early stage would provide enormous benefits for both the patient and the physician. It would permit the design of accurate treatment regimes, prevent unnecessary medications and reduce treatment costs. Even though the overall clinical picture in IBD patients may show some clinically important differences between the major patient groups of UC and CD, there are substantial similarities, thus making it difficult for health care personnel to establish a correct diagnosis.

PRIOR ART

The prior art indicates that the available methods for distinguishing between forms of IBD, and in particular the differentiation between UC and CD, apart from the above given examples of different examination procedures, have been focused on antibody based methods.

For example WO 03/036262 describes a method and apparatus for the differentiation of Crohn's disease from other gastrointestinal illnesses, such as ulcerative colitis and irritable bowel syndrome, using the presence of faecal anti-*Saccharomyces cerevisiae* antibodies (ASCA) as a marker for Crohn's disease are provided. The apparatus includes an enzyme-linked immunoassay or other immunoassay that utilizes antibodies specific to human immunoglobins for the measurement of total endogenous ASCA in a human faecal sample. The method and apparatus may be used by healthcare providers to distinguish Crohn's disease from other gastrointestinal illnesses, such as ulcerative colitis and irritable bowel syndrome.

WO 01/58927 describes diagnostic methods for detecting diseases associated with an autoantigen response to hTM in affected tissue, and in particular ulcerative colitis.

There remains a need for improved methods for the accurate, rapid and reliable diagnosis of ulcerative colitis, in particular in the context of distinguishing between ulcerative colitis and Crohn's disease in IBD patients.

One aim of the present invention is to make available such methods and kits for this purpose. One particular aim is to make available a method and kit which makes it possible to reach a reliable diagnosis at an early stage of the disease. Another aim is to make it possible to distinguish between CD and UC also in difficult cases, where the clinical picture may be very similar.

Further aims underlying the invention, as well as the solutions offered by the invention and the associated advantages will become evident to a skilled person upon study of the description, examples and claims.

SUMMARY OF THE INVENTION

The present inventors have surprisingly found that the differentiation between ulcerative colitis and Crohn's disease is made possible by a multi-gene approach where the gene expression profiles in biopsy samples obtained from inflamed and optionally also non-inflamed areas in the intestines of a patient are studied.

The present invention is based on the discovery of potential marker genes which, either collectively or in sub-groups, are indicative of the human condition of ulcerative colitis (UC). The present inventors surprisingly found that quantification of the expression levels of a number of specific genes can be utilized in accurately and simply diagnosing from a biopsy, whether the patient is afflicted with the condition of UC or, for example, Crohn's disease.

More specifically, methods are provided that allow nucleic acid amplification of seven (7) distinct genetic markers or sub-groups thereof, using pre-selected gene specific primers that allow for semi quantification of the expression levels of said genetic markers. The gene specific primers are designed to hybridise to opposing strands of the DNA encoding the genetic marker of interest such that though PCR amplification, a defined region of the encoding DNA of the genetic marker gene is produced. An assay and kit for the detection and monitoring expression status of said seven marker genes or sub-sets thereof in a biological sample are provided. The assay is a non-culture, PCR-based assay for the detection of said marker genes.

BRIEF DESCRIPTION OF THE DRAWINGS

The present invention will be described in closer detail in the following description and examples, with reference to the drawings in which.

DETAILED DESCRIPTION OF THE INVENTION

Figure 1:
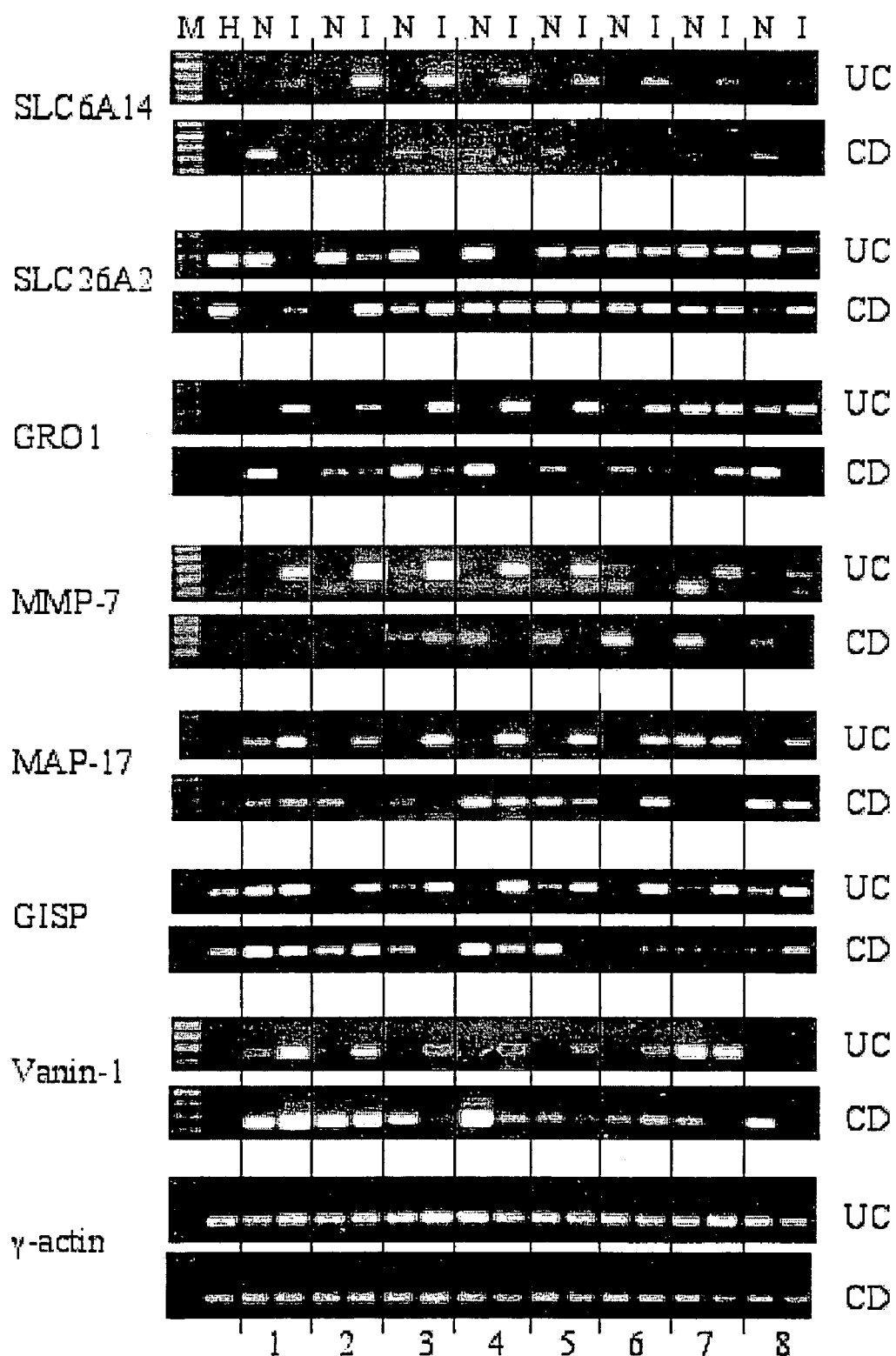
FIG. 1 shows the RT-PCR analysis of expression status of seven marker genes on biopsy samples from patients afflicted with either ulcerative colitis (UC) or with Crohn's Disease (CD). The experimental protocol is out-lined in Example 6. (Key: M, is a base-pair marker, H, represents a biopsy from a totally normal healthy individual, I, represents a biopsy sample taken from an inflamed area and N, represents a biopsy taken from a non-inflamed area from the same patient. Numbers at the bottom of the FIGURE indicates patient number and the vertical black lines indicate an N and I biopsy sample derived from the same patient). Gamma actin was used as a loading control and indicates the expression status of a house-keeping gene used commonly to demonstrate equal mRNA input in all RT-PCR reactions.

Before the present invention is disclosed and described, it is to be understood that one skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations of the scope of the invention. Changes therein and other uses that will occur to those skilled in the art are encompassed within the spirit of the invention as defined by the scope of the claims.

As used herein, the term "complementary DNA primer" means an oligonucleotide, which anneals to the RNA template in a particular orientation to allow for the synthesis of a nascent DNA strand in the presence of reverse transcriptase in the biological sample under the conditions described herein.

Also as used herein, the "condition" under which a DNA strand is synthesized include the presence of nucleotides, cations and appropriate buffering agents in amounts and at temperatures, such that the RNA template and the DNA primer will anneal and oligonucleotides will be incorporated into a synthesized DNA strand if reverse transcriptase is not inhibited by the reverse transcriptase inhibitor drug. Exemplary conditions are set forth in the examples below. The described conditions have been optimised from other known RT/cDNA synthesis protocols. It is generally known that other conditions can be established for optimisation of a particular reverse transcriptase reaction on the basis of protocols well known to one of ordinary skill in the art.

As used herein, the term "primer pair" refers to two primers, one having a forward designation and the other having a reverse designation relative to their respective orientations on a double-stranded DNA molecule which consists of a sense and antisense sequence, such that under the amplification conditions described herein, the forward primer anneals to and primes amplification of the sense sequence and the reverse primer anneals to and primes amplification of the antisense sequence. Primers can be selected for use in the amplification reaction on the basis of, having minimal complementarity with other primers in the reaction (to minimize the formation of primer dimers) and having Tm values with the range of reaction temperatures appropriate for the amplification method, preferably PCR. In addition, primers can be selected to anneal with specific regions of the RNA template such that the resulting DNA amplification product ranges in size from 100 to 500 base pairs in length and most preferably around 300 base pairs in length.

For example, in the conditions described above, the primer pair can consist of the oligonucleotide of SEQ ID NO: 13 as the forward primer and the oligonucleotide of SEQ ID NO: 14 as the reverse primer.

As used herein, the terms "detecting" or "detection" of the amplified DNA refers to qualitatively or quantitatively determining the presence of the amplified DNA strand, which is only synthesized if reverse transcriptase is resistant to the reverse transcriptase inhibitor drug added to the assay mixture. The amplification of the synthesized DNA can be detected by any method for the detection of DNA known in the art. For example, detection of the amplified DNA can be by Southern blot hybridisation assay, by visualization of DNA amplification products of specific molecular weight on ethidium bromide stained agarose gels, by measurement of the incorporation of radiolabeled nucleotides into the synthesized DNA strand by autoradiography or scintillation measurement.

The preferred detection method is by agarose gel electrophoresis using ethidium bromide staining and visualisation under UV light.

The principles of PCR and the conditions for amplification and detection of target nucleic acids are well known in the art and may be found in numerous references known to the skilled artisan, including, for example, U.S. Pat. No. 4,683,195; U.S. Pat. No. 4,683,202 and U.S. Pat. No. 4,965,188; all to Mullis et al. Briefly, a sample suspected of containing a target nucleic acid is heated to denature double-stranded nucleic acid in the presence of two oligonucleotide primers that are complementary to target sequences flanking the region to be amplified. The primers anneal to the separated target strands and are extended from each 3' hydroxyl end by a polymerising agent such as a thermostable polymerase. Double-stranded or single-stranded DNA can be amplified by PCR. RNA can also serve as a target by reverse transcribing RNA into cDNA.

The steps of denaturation, primer annealing and DNA synthesis are carried out at discrete temperatures, and repeated cycles result in exponential accumulation of the target nucleic acid. The PCR vessel is generally a stoppered plastic vessel or a cuvette or pouch as described in U.S. Pat. No. 5,229,297. Reagents for PCR amplification are typically mixed in a single vessel, and generally include primers, nucleoside triphosphates (generally dATP, dCTP, dGTP and dTTP or dUTP), thermostable DNA polymerase, magnesium containing buffer, and target nucleic acid. Reagents and conditions for PCR are well-known to one of ordinary skill in the art, and can be found, for example, in Guatelli et al. (1989) Clin. Microbiol. Rev. 2:217. For amplification of RNA targets, a reverse transcriptase may be utilized in addition to or in lieu of the thermostable DNA polymerase. Thermostable reverse transcriptase are particularly useful, as are thermostable DNA polymerases having reverse transcriptase activity. Methods for PCR amplification of RNA targets are known to one of ordinary skill in the art and described, for example, in U.S. Pat. Nos. 5,176,995, 5,310,652 and 5,322,770.

Detection of the DNA amplified by the PCR is generally conducted in a manner that the DNA is subjected to electrophoresis using agarose gel, acryl amide gel or the like, and then it is subjected to dyeing with nucleic acid-specific dyeing reagents. In the case of detecting double-stranded DNA, usually a fluorescent reagent such as ethidium bromide is allowed to enter between two strands of the DNA and then the fluorescent reagent is excited by an ultraviolet light source. As ethidium bromide entered between the two strands of the DNA emits fluorescence, detection is performed by means of capturing the fluorescence with a CCD camera or the like.

The object of the present invention is accomplished by the amplification, by PCR, of seven specific marker genes or sub-sets thereof and latter separation by electrophoresis of the products of this amplification, followed by appropriate colouring techniques that permit an adequate visualisation of the DNA in the gel including, but not limited to: colouring by silver salts, radioisotopes and enzymes combined with substrates that permit their detection.

It is an object of certain embodiments of the present invention to provide a method of conducting nucleic acid amplification reactions in a single reaction chamber whereby internal primer pairs hybridise to opposing reigns of said target genetic marker genes, and amplification occurs by polymerase chain reaction.

Internal control primer pairs designed to hybridise to opposing strands of a suitable control housekeeping gene such that semi-quantitative comparisons can be made. Such a preferred housekeeping gene can be actin, GADPH, or elongation factors. By measuring the intensity of the internal control signal and comparing that to the signals given by the said genetic marker genes, one can determine the degree of change of expression of said genetic marker gene from the normal levels of expression (i.e. those levels in which no disease state is present).

In the method of the present invention, PCR amplification is accomplished by pre-incubating all PCR reagents and a sample containing a target nucleic acid in the presence of appropriate gene specific primers and a thermostable polymerase enzyme. The resulting reaction mixture is cyclically heated under conditions allowing for the formation and amplification of primer extension products.

The reagents required for PCR are known to persons skilled in the art, and generally include at least two oligonucleotide primers that are sufficiently complementary to conserved regions of the target nucleic acid to hybridise thereto, four different nucleoside triphosphates, a thermostable polymerisation agent and any requisite cofactors for the polymerisation agent. Preferred nucleoside triphosphates are the deoxyribonucleoside triphosphates dATP, dCTP, dGTP and dTTP or dUTP, collectively termed dNTPs. Nucleoside triphosphates are commercially available.

Primers include naturally occurring or synthetically produced oligonucleotides capable of annealing to the target nucleic acid and acting as the point of initiation of nucleic acid synthesis under appropriate conditions, i.e., in the presence of nucleoside triphosphates, a polymerisation agent, suitable temperature, pH and buffer. The primers have sequences sufficiently complementary to the target nucleic acid to hybridise thereto, and are of sufficient length, typically from 10-60 nucleotides, to prime the synthesis of extension products in the presence of a polymerisation agent. Primers may be produced synthetically by automated synthesis by methods well known to one of ordinary skill in the art.

Design considerations for primers are well known in the art. Primers are selected to be substantially complementary to the sequences of the strands of the specific nucleic acid to be amplified, such that the extension product synthesized from one primer, when separated from its complement, can serve as a template for the extension product of the other primer. Preferably, the primers are exactly complementary with the target region. It is underlined that the primer pairs given in the present specification, examples and claims can be replaced by functionally equivalent primers, exhibiting specificity to the marker genes, without departing from the scope of the invention.

The inventors have unexpectedly identified seven (7) marker genes whose specific changes in expression status, collectively or in sub-sets, is indicative of the inflammatory bowel disease condition, UC. This opens the possibility of a rapid detection protocol at the molecular level designed to aid the examining physician in correctly predicating disease type.

The expression profile in inflamed and non-inflamed tissue is exemplified in FIG. 1 and in Table 1 below.

TABLE 1

Expression profiles in inflamed and non-inflamed tissue

| Marker gene | Inflamed tissue | | Non-inflamed tissue | |
| --- | --- | --- | --- | --- |
| | Ulcerative colitis | Crohn's disease | Ulcerative colitis | Crohn's disease |
| SLC6A14 | X | — | — | X |
| SLC26A2 | — | X | XX | X |
| GRO1 | X | — | — | X |
| MMP-7 | XX | — | X | — |
| MAP-17 | X | — | — | X |
| GISP | XX | X | X | XX |
| Vanin-1 | X | (X) | — | X |
| Gamma actin (control) | X | X | X | X |

X, and XX indicates the degree of expression; (X) indicates a result which is likely to be disregarded in light of the overall picture; — denotes lack of expression The genetic markers are solute carrier family 6 member 14 (SLC6A14), solute carrier family 26 member 2 (SLC26A2), CXC chemokine growth-related oncogene-alpha (Gro-alpha) or (CXCL-1), Matrilysin also known as matrix metalloproteinase-7 (MMP-7), gastro-intestinal secretory protein (GISP) also know as regenerating gene type IV (Reg IV), membrane associated protein 17 (MAP-17), and vanin-1. See Table 2.

TABLE 2

Target genetic marker genes

SEQ. ID. NO. 1 (GeneBank Acc No NM-007231)
SEQ ID NO:2 (GeneBank Acc No NM-000112)
SEQ ID NO:3 (GeneBank Acc No NM-001511)
SEQ ID NO:4 (GeneBank Acc No BC003635)
SEQ ID NO:5 (GeneBank Acc No NM-005764)
SEQ ID NO:6 (GeneBank Acc No BC017089)
SEQ ID NO:7 (GeneBank Acc No NM-004666)

Polymerisation agents are compounds that function to accomplish the synthesis of the primer extension products. The polymerisation agents are thermostable, i.e., not permanently inactivated when heated for brief periods to temperatures typically used in PCR for denaturation of DNA strands, e.g., 93-95° C., and are preferentially active at high temperatures. In a preferred embodiment the polymerisation agent is a thermostable DNA polymerase, including, for example, DNA polymerase obtained from thermophilic bacteria such as, *Thermococcus litoralis, Bacillus stearothermophilus, Methanothermus fervidus, Thermus aquaticus, T. filiformis, T. flavus, T. lacteus, T. rubens, T. ruber* and *T. thermophilus*, or from thermophilic archaebacteria such as *Desulfurococcus mobilis, Methanobacterium themmoautotrophilcum, Sulfolobus solfataricus, S. acidocaldarius* and *Thermoplasma acidophilum*. In a most preferred embodiment, the polymerisation agent is *Thermus aquaticus* (Taq) polymerase, *T. thermophilus* (Tth) polymerase or *Thermococcus litoralis* polymerase. Thermostable reverse transcriptase and DNA polymerases having reverse transcriptase activity are also contemplated as polymerisation agents.

The thermostable polymerases may be obtained commercially or by methods known in the art. In particular, Taq polymerase is available commercially in recombinant and native form (Perkin Elmer-Cetus) or can be produced by the method described by Lawyer et al., (1989) or in U.S. Pat. No. 4,889,818. Tth polymerase is commercially available from Finnzyme Co., Finland and from Toyobo Co., Japan. *Thermococcus litoralis* polymerase is commercially available from New England Biolabs and can be produced by the method described in U.S. Pat. No. 5,322,785.

Antibodies specific for the thermostable polymerisation agents may be included in the pre-amplification step to inhibit the polymerisation agent prior to amplification. Antibodies can be produced by methods known to one of ordinary skill in the art and found, for example, in Harlowe et al. (1988) Antibodies: A Laboratory Manual, Cold Spring Harbor, N.Y. In accordance with the present invention, the term antibodies includes monoclonal and polyclonal antibodies produced by conventional methodologies, recombinantly produced antibodies, and chemically or recombinantly produced fragments of antibodies, such as Fab fragments. In a preferred embodiment, the antibodies are monoclonal.

In a preferred embodiment of the present invention, the antibody is a monoclonal antibody against Taq polymerase, Tth polymerase, or *Thermococcus litoralis* polymerase. In a more preferred embodiment, the antibody is a monoclonal antibody against Taq polymerase. Monoclonal antibodies against Taq polymerase are known in the art and described, for example, in U.S. Pat. No. 5,338,671. In accordance with the present invention, antibodies defined as specific for polymerisation agent are those antibodies that are capable of inhibiting the enzymatic activity of the polymerisation agent at temperatures from about 20-40° C. The antibodies of the invention are inactivated by elevated temperatures used during PCR thermal cycling. The ability of the antibodies to inhibit enzymatic activity of the polymerase can be determined by assays known to one of ordinary skill in the art, as described, for example, by Sharkey et al., (1994).

The present invention provides a method for the amplification of a target nucleic acid, and optionally, the subsequent detection of the nucleic acid, in a sample suspected of containing the target nucleic acid. The sample may be any sample suspected of containing a target nucleic acid, including, for example, a tissue sample, blood, hair, body fluid, bacteria, virus, fungus, bacterial infected cell, virally infected cell, and so on. The target nucleic acid may be DNA or RNA. A sufficient number of bases at both ends of the sequence to be amplified must be known in order to design primers capable of hybridising to the different strands of the target nucleic acid at suitable positions for PCR amplification. The target nucleic acid may be extracted or partially extracted from the tissue sample prior to PCR, for example, by removing proteins or cellular material from the sample. Methods for extracting nucleic acids from samples are known to one of ordinary skill in the art and may be found, for example, in Sambrook et al., (1989) and Saiki et al., (1985).

In a preferred embodiment, biopsies resected from the gastro-intestinal tract and from area believed to be exhibiting signs of the disease is particularly preferred as the source of material.

In the method of amplification of the present invention, the sample or a preparation of nucleic acids extracted from the sample is contacted with the reagents typically used for PCR, including at least two oligonucleotide primers modified to contain at least one phosphorothioate linkage, four different nucleoside triphosphates, a thermostable polymerisation agent, and an appropriate buffer, and further with an exonuclease to form a reaction admixture. In another embodiment, an antibody specific for the polymerisation agent is included in the admixture.

The conventional PCR reagents, including primers, nucleoside triphosphates, polymerisation agent, and appropriate buffer are utilized at concentrations generally appropriate for PCR and known to one of ordinary-skill in the art. In a preferred embodiment, the nucleoside triphosphates are dATP, dCTP, dGTP and dTTP. In a preferred embodiment the polymerisation agent is a thermostable DNA polymerase. Preferred DNA polymerases are Taq polymerase, Tth polymerase and *Thermococcus litoralis* polymerase. Taq polymerase is particularly preferred.

The amplification method is preferably conducted in a continuous, automated manner. Appropriate instrumentation for automated PCR is well-known to the ordinarily skilled artisan and described, for example, in U.S. Pat. Nos. 4,965,188, 5,089,233 and 5,229,297. The skilled artisan can also easily detect amplified product, for example, by separating PCR products by agarose gel electrophoresis and visualizing by ethidium bromide staining, or detecting by hybridisation with a labeled probe capable of hybridising with the amplified nucleic acid or a variety of other detection methods well-known to one of ordinary skill in the art.

One embodiment of the invention is thus a method for the differentiation between ulcerative colitis and Crohn's disease based on the analysis of gene expression profiles in biopsy samples obtained from inflamed and non-inflamed areas in the intestines of a patient, wherein the expression levels of at least two of a number of marker genes are determined, said at least two marker genes chosen among SEQ ID NO:1, SEQ ID NO:2, SEQ ID NO:3, SEQ ID NO:4, SEQ ID NO:5, SEQ ID NO:6, and SEQ ID NO:7.

Another embodiment of the invention is a method wherein the expression levels of SEQ ID NO:1 and SEQ ID NO:2 are determined and wherein the expression of SEQ ID NO:1 in inflamed tissue and lack of expression in non-inflamed tissue, together with the lack of expression of SEQ ID NO:2 in inflamed tissue is taken as an indication of ulcerative colitis.

A third embodiment of the invention is a method wherein the expression levels of SEQ ID NO:1, SEQ ID NO:2, and, SEQ ID NO:3 are determined, and wherein the expression of SEQ ID NO:1 in inflamed tissue and lack of expression in non-inflamed tissue, together with the lack of expression of SEQ ID NO:2 in inflamed tissue, and the expression of SEQ ID NO:3 in inflamed tissue and lack of expression in non-inflamed tissue, is taken as an indication of ulcerative colitis.

A fourth embodiment is a method wherein the expression levels of SEQ ID NO:1, SEQ ID NO:2, and SEQ ID NO:4 are determined, and wherein the expression of SEQ ID NO:1 in inflamed tissue and lack of expression in non-inflamed tissue, together with the lack of expression of SEQ ID NO:2 in inflamed tissue, and the expression of SEQ ID NO:4 in inflamed tissue and lack of expression in non-inflamed tissue, is taken as an indication of ulcerative colitis.

A fifth embodiment is a method wherein the expression levels of SEQ ID NOs:1-7 are determined, and wherein the expression of SEQ ID NO:1, SEQ ID NO:3, SEQ ID NO:4, SEQ ID NO:5, SEQ ID NO:6, and SEQ ID NO:7 in inflamed tissue and lack of expression in non-inflamed tissue, together with the lack of expression of SEQ ID NO:2 in inflamed tissue, is taken as an indication of ulcerative colitis.

According to a preferred embodiment, the method of any one of the above embodiments includes a step wherein the expression level of each marker gene is determined through nucleic acid amplification of said genes using gene specific primers, and determination of the amplification results. The nucleic acid amplification is preferably performed using PCR and the gene specific primers preferably chosen among SEQ ID NOs:13-26.

The determination of the amplification results is preferably performed using ethidium bromide staining and visualisation under UV light.

The present invention further provides a kit for PCR comprising, in the same or separate containers, a thermostable polymerisation agent, and primer pairs designed to allow PCR amplification of said target genes. Additional containers can also be provided for the inclusion of, for example, additional antibodies specific to the PCR polymerisation agent and reagents for PCR, including, for example, nucleoside triphosphates, primers and buffers.

Consequently, the present invention makes available a kit for the differentiation between ulcerative colitis and Crohn's disease based on the analysis of gene expression profiles in biopsy samples obtained from inflamed and non-inflamed areas in the intestines of a patient, said kit including gene specific primer pairs directed to at least two marker genes chosen among SEQ ID NO:1, SEQ ID NO:2, SEQ ID NO:3, SEQ ID NO:4, SEQ ID NO:5, SEQ ID NO:6, and SEQ ID NO:7.

Said gene specific primer pairs are preferably chosen among SEQ ID NO:13 and SEQ ID NO:14; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; and SEQ ID NO:25 and SEQ ID NO:26.

According to one embodiment of the invention, said specific primers are SEQ ID NO:13 and SEQ ID NO:14; SEQ ID NO:15 and SEQ ID NO:16; and SEQ ID NO:17 and SEQ ID NO:18.

According to another embodiment of the invention, said specific primers are SEQ ID NO:13 and SEQ ID NO:14; SEQ ID NO:15 and SEQ ID NO:16; and SEQ ID NO:19 and SEQ ID NO:20.

The kit according to the invention further preferably comprises a thermostable polymerisation agent and requisite cofactor(-s). In a preferred embodiment the polymerisation agent is a DNA polymerase. In a more preferred embodiment the polymerase is Taq polymerase, Tth polymerase, or *Thermococcus litoralis* polymerase. Taq polymerase is particularly preferred. The preferred antibody is a monoclonal antibody specific for Taq polymerase.

The oligonucleotide primers preferably are 19-25 nucleotides in length and are designed as primer-pairs that will under standard conditions anneal to the target DNA of said genetic marker genes. In this case seven primer pairs are provided that will allow successful amplification of the seven said genetic marker genes. The specific primers used are presented in Table 3.

TABLE 3

Primer-pairs

| | | |
|---|---|---|
| SLC6A14 (for) | 5'-GTG CTG AGA TTA CAG GTG TGA GCC-3' | (SEQ ID NO:13) |
| SLC6A14 (rev) | 5'-CCC TTC ACA CCT CCC CCA ATT AGA-3' | (SEQ ID NO:14) |
| SLC26A2 (for) | 5'-GTG GAG AGA GGG AAA GAA TGT TGC-3' | (SEQ ID NO:15) |
| SLC26A2 (rev) | 5'-CCA GTT TAG GAC AGA TTC CAT GGG-3' | (SEQ ID NO:16) |
| GRO1 (for) | 5'-GTG CCT AAT GTG TTT GAG CAT CGC-3' | (SEQ ID NO:17) |
| GRO1 (rev) | 5'-GCC CCT TTG TTC TAA GCC AGA AAC-3' | (SEQ ID NO:18) |
| MMP7 (for) | 5'-CAG GCA GAA CAT CCA TTC ATT CAT TC-3' | (SEQ ID NO:19) |
| MMP7 (rev) | 5'-GAC ATC TAC CCA CTG CAA GTA TAG-3' | (SEQ ID NO:20) |
| MAY17 (for) | 5'-CCG TCG GAA ACA AGG CAG ATG GAG-3' | (SEQ ID NO:21) |

TABLE 3-continued

Primer-pairs

| | | |
|---|---|---|
| MAY17 (rev) | 5'-GAA GGA CGT GTG AGC AGG ATG GGA-3' | (SEQ ID NO:22) |
| GISP (for) | 5'-GGT GGG AAC AAG CAC TGT GCT GAG-3' | (SEQ ID NO:23) |
| GISP (rev) | 5'-GGC TGG AGA TGC ACT CTT CTA GAC-3' | (SEQ ID NO:24) |
| Vanin1 (for) | 5'-GCC AGC AAA ACA TCA TTT TGA GAC-3' | (SEQ ID NO:25) |
| Vanin1 (rev) | 5'-GCC TAT CAC CAA CAC ATC AAT ATG-3' | (SEQ ID NO:26) |

The genetic markers disclosed are, solute carrier family 6 member 14 (SLC6A14), as given by SEQ ID NO:1, solute carrier family 26 member 2 (SLC26A2) as given by SEQ ID NO:2, CXC chemokine growth-related oncogene-alpha (Gro-alpha) or (CXCL-1) as given by SEQ ID NO:3, Matrilysin also known as matrix metalloproteinase-7 (MMP-7) as given by SEQ ID NO:4, gastro-intestinal secretory protein (GISP) also know as regenerating gene type IV (Reg IV) as given by SEQ ID NO:5, membrane associated protein 17 (MAP-17) as given by SEQ ID NO:6, and Vanin-1 as given by SEQ ID NO:7. See Table 2, supra.

In the methods illustrated by the examples, a number of method based sequences were used. These are presented in Table 4.

TABLE 4

Method based sequences

| | |
|---|---|
| (SEQ ID NO:8) | 5'-TAG TCT ATG ATC GTC GAC GGC TGA TGA AGC GGC CGC TGG AGT TTT TTT TTT TTT TTT TTV-3' |
| (SEQ ID NO:9) | 5'-TGA TGA AGC GGC CGC TGG-3' |
| (SEQ ID NO:10) | 5'-TTC ATC AGC CGT CGA CGA TC-3' |
| (SEQ ID NO:11) | 5'-CGT AAG CTT GGA TCC TCT AGA GC-3' |
| (SEQ ID NO:12) | 5'-TGC AGG TAC CGG TCC GGA ATT CC-3' |

Solute carrier (SLC) proteins comprise of a very large family of energy dependent transport molecules and have critical physiological roles in nutrient transport and may be utilized as a mechanism to increase drug absorption. However, there is limited understanding of these proteins at the molecular level due to the absence of high-resolution crystal structures.

In total, 1-2% of adults and 6-8% of children suffering from kidney stones have cystinuria, a defect in the transport of amino acids, which leads to high concentrations of cystine in the urine. Two genes have been implicated, solute carrier family 3 (cystine, basic and) neutral amino acid transporter, member 1 (SLC3A1) coding for the protein related to the system of amino-acid transporter, and solute carrier family 7, member 9 (SLC7A9). Both of these solute carriers are believed to be involved in stone formation which may ultimately lead to urinary tract infection and, eventually, renal failure.

The inventors have identified two known solute carriers (SLC6A14 and SLC26A2) whose expression is significantly altered in IBD. To the best knowledge of the inventors, this is the first reporting of the potential involvement of solute carriers in inflammatory bowel diseases. It is therefore a novel finding that solute carriers might contribute to the pathogenesis of IBD.

CXC chemokine growth-related oncogene-alpha (Gro-alpha also known as GRO1) is as described a cytokine and as such can alter the migratory responses of numerous cell types in local areas of inflammation. It and has been described to be over expressed in human inflamed corneas (Spandau et al., 2003) and in addition, it has also been shown that rats chemically induced to exhibit inflammation of the gut show up-regulated levels of GRO1 (Hirata et al., 2001). Using a cDNA microarray approach, Heller et al., 1997 describes novel participation of the, chemokine Gro alpha in rheumatoid arthritis and inflammatory bowel disease, however the invention presented here describes, in the inventors best knowledge for the first time, that GRO1 while over expressed in conditions of UC is down regulated in conditions of CD. While it is described in Isaacs et al, 1992, that expression of GRO1 in UC is higher than that seen in CD, here it has been demonstrated that there exists an inverse correlation of UC verses CD with respect to GRO1 expression levels. Lastly Lawrence et al., 2001 describes identifying GRO1 as being up-regulated in UC, but the design of the study was such that biopsy samples where pooled before analysis, therefore is was not possible to know whether GRO1 was up-regulated in more than 1 patient.

Matrilysin or (matrix metalloproteinase-7) was first discovered in the involuting rat uterus; it has also been known as uterine metalloproteinase, putative metalloproteinase (Pump-1), and matrix metalloproteinase 7 (MMP-7). It is the smallest member (28 kDa) of a family of 15 MMPs that together are able to degrade most of the macromolecules of the extra cellular matrix. This family is briefly reviewed; all members are zinc metalloproteinases that occur in zymogene form with the active site zinc blocked by cysteine. Matrilysin can degrade a wide range of gelatins, proteoglycans, and glycoproteins of the matrix and can activate several other MMPs including collagenase (reviewed in Woessner, 1996).

It is frequently expressed in various types of cancer including colon, stomach, prostate, and brain cancers. Previous studies have suggested that matrilysin plays important roles in the progression and metastasis of colon cancer. Recently it has been described by Newell et al., 2002 that there is an increase of matrilysin expression at different stages of UC-associated neoplasia. This work however does not determine whether such increased expression is a result of UC or rather due to the presence of neoplasia.

Membrane associated protein 17 (MAP-17) or otherwise know as DD96, is a small protein has to date no described function. Regarding GISP, again there is little known. In both cases neither has been described as potentially involved in inflammation.

Pantetheinase (EC 3.5.1.) is an ubiquitous enzyme which in vitro has been shown to recycle pantothenic acid (vitamin B5) and to produce cysteamine, a potent anti-oxidant. The enzyme is encoded by the Vanin-1 gene and is widely expressed in mouse tissues. Vanin-1 is a GPI-anchored pantetheinase, and consequently an ectoenzyme. It has been suggested that Vanin/pantetheinase might be involved in the regulation of some immune functions maybe in the context of the response to oxidative stress (Pitari et al., 2000).

To the best knowledge of the inventors, this is the first description of the potential role of Vanin-1 in IBD.

While the present invention has been described with specificity in accordance with certain of its preferred embodiments, the following examples are only intended to illustrate the invention and not to limit the same. While they are typical of methods and method steps that might be used, others known to those skilled in the art may be adopted without resorting to undue experimentation.

EXAMPLES

Example 1

Collection of Biopsy Material

The biopsies were taken from patients who were selected on the basis of clinical and pathological evidence of having the inflammatory condition of CD or UC. A total of three biopsies were collected from an inflamed site in the colon, together with three biopsy samples from a non-inflamed region of a single individual patient. This was done for a total of 16 different patients of which eight were diagnosed for CD (patient 1-8) and eight for UC (patient 9-16). The UC patient group comprised 2 females and 6 males, the age range being 29-77 years. The CD age group correspondingly 3 females and 5 males, age range 27-59.

The biopsies from each anatomical site of one patient were pooled and total RNA isolated using Qiagen RNEASY Kit, RNA isolation kit, and a Pellet Pestel Motor Homogenizer according to the manufacturer's protocol. In this way 32 samples of total RNA were isolated, two samples per patient: inflamed (target) and non-inflamed (control).

Example 2

Performing cDNA Synthesis of the RNA

Two microgram of each RNA sample (32 in total) was used for a first strand cDNA synthesis using 10 pM of the Oligo-dT-primer dT-joint (5'-TAG TCT ATG ATC GTC GAC GGC TGA TGA AGC GGC CGC TCG AGT TTT TTT TTT TTT TTT TTV-3' (SEQ ID NO:8) introducing to every synthesised cDNA molecule three restriction enzyme cutting sites: SalI, NotI and BpmI. The buffer, desoxynucleotide triphosphates (dATP, dCTP, dGTP and dTTP) and the enzyme reverse transcriptase (SUPERSCRIPT II) were taken from Gibco BRL and the reactions were performed according to the manufacturer's guidelines. The reaction mixture for first strand synthesis excluding the enzyme was pre-incubated for 5 min at 65° C. in a PCR machine (PCR sprint from Hybaid), chilled on ice, and then preheated to 42° C., before the enzyme SUPERSCRIPT II, reverse transcriptase, was added and incubated for 1 h at 42° C. in a PCR machine (PCR sprint from Hybaid).

For the second strand synthesis, 41 µl second strand buffer mix were added to the reactions according to the provided protocol (Gibco BRL) and 4 µl E. coli Polymerase I (New England Biolabs), 1.5 µl E. coli DNA ligase (New England Biolabs) and 0.7 µl Rnase H (Gibco BRL) in a total volume of 160 µl. The reactions were incubated for 2.5 h at 16° C. in the PCR machine PCRsprint and then purified using the Qiagen PCR Purification Kit according to the protocol provided. Every sample (32 in total) was eluted with 32 µl of elution buffer and 26 µl of each sample was used for the following steps.

Example 3

Amplification of the 3'-Termini of the cDNAs

Due to limited amounts of material obtained from such biopsies, a pre-amplification step was necessary. For in vitro amplification of the 3'-end of cDNAs, 26 µl of cDNA from every sample was digested with 10U of the restriction enzyme DpnII in a volume of 30 µl for 3 h at 37° C. The cut cDNAs were purified once more using Qiagen PCR purification Kit and the cDNAs were eluted in 47 µl elution buffer. The following circular ligation step was performed in a volume of 50 µl including 44 µl of the DpnII cut cDNA and 2000U T4 DNA ligase (New England Biolabs). These reaction mixtures were incubated at 22° C. for 1 h, heat inactivated by 65° C. for 10 min and 25 µl of each reaction mixture was used for the amplification step. A mixture for 5 reactions per sample was put together (5×50 µl=250 µl in total) containing 25 µl cDNA (DpnII cut and circular ligated), 25 µl 10× Advantage 2 PCR buffer (Clontech), 5 µl joint-Not primer (10 pmol/µl; 5'-TGA TGA AGC GGC CGC TGG-3' (SEQ ID NO:9)), 5 µl joint-Sal primer (10 pmol/µl —5'-TTC ATC AGC CGT CGA CGA TC-3' (SEQ ID NO:10), 5 µl 10 mM dNTP mix and 5 µl 50× Advantage 2 Taq-Polymerase (Clontech). For each sample the mix was distributed into 5 PCR reaction tubes and PCR performed under the following conditions: 1 min 94° C. then 16× (20 sec 94° C., 20 sec 55° C., 1 min 72° C.).

Four of the reactions per sample were removed and placed on ice and the optimal cycle number was determined with one of the reactions per sample. The optimal cycle number was determined to 18 cycles for all 32 samples, thus for the remaining four reactions per sample two additional cycles [2× (20 sec 94° C., 20 sec 55° C., 1 min 72° C.)] were performed. The 4 PCR reactions per sample were subsequently purified using the Qiagen PCR purification Kit. For the purification, the four reactions per sample were pooled (total of 200 µl) and then eluted with 34 µl elution buffer. The purified reactions were the starting material for the identification of the differentially expressed genes protocol.

Example 4

Isolation of the Differentially Expressed cDNA (Subtraction Protocol) from Human Biopsies Isolation of differentially expressed cDNAs was performed according to the protocol outlined in (von Stein O. D., 2001) with minor modifications to the protocol.

Example 5

Screening for the Differentially Expressed Genes

Upon construction of a cDNA library, 2.000 clones were plated out from each subtraction on one 22 cm² agar plate. From these plates 384 colonies were picked and placed in 384 well plates with 70 µl LB medium/well (see Maniatis et al., Molecular cloning laboratory book, Appendix A. 1) (+ampicillin 100 mg/ml) using BioPick machine of BioRobotics (Cambridge, UK). The bacterial clones were incubated over night at 37° C. and then used for colony PCR. This PCR was performed in 384 PCR well plates in a volume of 20 µl per sample. One PCR reaction included: 2 µl 10×PCR buffer, 0.4 µl Sport-Not primer (10 pmol 5'-CGT AAG CTT GGA TCC TCT AGA GC-3' (SEQ ID NO:11), 0.4 µl of Sport-Sal primer (10 pmol 5'-TGC AGG TAC CGG TCC GGA ATT CC-3' (SEQ ID NO:12)), 1.6 µl dNTP mix (25 mM each), 0.4 µl 0.1% Bromphenol blue and 0.5 µl DynAzyme Taq-polymerase (2 U/µl; Finnzyme). A master mix for all reactions was prepared, distributed and then inoculated with a 384 plastic replica. The PCR cycling parameters were: 2 min 94° C., 37 times (30 sec 94° C.; 30 sec 50° C., 1 min 72° C.) and 5 min 72° C.

Following amplification, PCR reactions were spotted on HYBOND N+ membrane (Amersham) using Microgrid TAS of BioRobotics. All clones were spotted in duplicate and genomic DNA was used as guide dots. On one filter 384 genes of all four subtractions were positioned. 24 duplicates were made for analyses by hybridisation with different radioactive cDNA probes.

These filters were then hybridised with the radioactive labeled subtracted cDNAs of all eight patients. Sixteen filters were used in 16 different hybridisation experiments. For that 1 µl of the cDNAs were used for the labelling with Klenow polymerase. The hybridisation protocol was that of Church-protocol as outlined in (Maxam and Gilbert 1984).

Phospho-imager Fuji film BAS 1800II with BAS 1800 III R program and ARRAYVISION version 6.0 (Imaging Research Inc) were used to determine the degree of differentially expression. Genes which were differentially expressed in at least three of the eight patients with an induction or reduction rate of three fold were sequenced and BLAST analysis performed to identify these isolated differentially expressed genes.

Example 6

Confirmation of True Differential Expression

Several genes showed strong dysregulation during these analyses. To confirm these data RT-PCR were performed using gene-specific oligonucleotides and un-amplified cDNA material derived from the same eight patients. Approximately, 21 µg total RNA of inflamed and non-inflamed tissue (same as used for the subtraction) were taken for a first strand cDNA synthesis as described in example 5. After the cDNA synthesis the samples were incubated for 3 min at 96° C. and then 1:10 diluted with distilled water.

10 µl of further 1:10 dilutions were taken for one 50 µl PCR reaction. The PCR reaction included: 5 µl 10×PCR buffer, 1 µl forward primer (10 pmol/µl) and 1 µl reverse primer (10 pmol/µl) of the specific genes (SEQ ID NOs:1-7)), 0.5 µl dNTP mix (25 mM each) and 0.5 µl DynAzyme Taq-polymerase (2 U/µl; Finnzyme). A master mix minus the cDNA for the reactions was prepared, distributed and then the cDNA added. The PCR cycling parameters were: 1 min 94° C., 26-35 times (30 sec 94° C.; 30 sec 55° C., 1 min 72° C.) and 5 min 72° C. The cycle number was dependent which gene fragments were amplified. The primer pairs were those shown in Table 3.

These analyses lead to the identification of seven (7) genetic markers whose change in expression status, collectively or in sub-sets, when compared to normal tissue would allow for a correct predication rate of over 90% with regard to UC. To confirm these findings, the markers where further screened against a larger sample collection of biopsies.

Example 7

High Throughput Screening

To confirm the preliminary results of the RT-PCR using the cDNA of eight UC patients and three CD patients (see Example 6), it was decided to analyse the expression of all isolated genes in a large scale. For that purpose, all genes that could be isolated from the screening were spotted on a Hybond N+ membrane (Amersham) using the Microgrid TAS (BioRobotics). As described in Example 5 the genes were amplified via a colony PCR for the spotting.

This master filter membrane was then synthesized 240 times and hybridised with radioactive labelled cDNA deriving from biopsies from 50 individual UC patients and 50 individual CD patients. The biopsies were taken from the inflamed and non-inflamed area of the patients in the left side of the colon. As a baseline control the biopsies deriving from the left side of the colon of five healthy people were pooled.

Example 8

Verification Through Blind Study

To provide greater statistical weight, it was necessary to perform expression analyse of the seven genetic markers on "blind" biopsy samples, whereby it was not known whether the biopsy was derived from a patient suffering from UC or CD. As described previously, RT-PCR analysis of the said genetic markers was performed and by combining the total picture of expression patterns resulting from said genetic markers it was possible to determine with over 90% certainty the correct form of IBD.

Analysis of the results (Blind study) show that already the combination of SEQ ID NOs:1 and 2 give a reliable result, whereas the combination of SEQ ID NOs:1, 2 and 3 or the combination of SEQ ID NOs:1, 2, and 4 give a further improved result. The preliminary results indicate that an accuracy of about 90% was reached using combination of SEQ ID NOs:1, 2, 3 and 4. It was shown that the use of the complete set of SEQ ID NOs: 1 through 7 resulted in an accuracy of more than 90%.

Although the invention has been described with regard to its preferred embodiments, which constitute the best mode presently known to the inventors, it should be understood

REFERENCES

Breuning M H, Hamdy N A (2003). From gene to disease; SLC3 μl, SLC7A9 and cystinuria. Ned Tijdschr Geneeskd. 147:245-7

Guatelli J C, Gingeras T R, Richman D D (1989). Nucleic acid amplification in vitro: detection of sequences with low copy numbers and application to diagnosis of human immunodeficiency virus type 1 infection. Clin Microbiol Rev. 2:217-26.

Harlowe E and Lane D (1989). Antibodies. A laboratory manual, Cold Spring harbour, NY Heller R A, Schena M, Chai A, Shalon D, Bedilion T, Gilmore J, Woolley D E, Davis R W (1997). Discovery and analysis of inflammatory disease-related genes using cDNA microarrays. Proc Natl Acad Sci USA. 94:2150-5.

Hirata I, Murano M, Nitta M, Sasaki S, Toshina K, Maemura K, Katsu K (2001). Estimation of mucosal inflammatory mediators in rat DSS-induced colitis. Possible role of PGE(2) in protection against mucosal damage. Digestion. 63 Suppl 1:73-80

Isaacs K L, Sartor R B, Haskill S (1992). Cytokine messenger RNA profiles in inflammatory bowel disease mucosa detected by polymerase chain reaction amplification. Gastroenterology. 103:1587-95

Lawrance I C, Fiocchi C, Chakravarti S (2001). Ulcerative colitis and Crohn's disease: distinctive gene expression profiles and novel susceptibility candidate genes. Hum Mol. Genet. 10:445-56.

Lawyer, F. C., Stoffel, S., Saiki, R. K., Myambo K, Drummond R, Gelfand D H (1989). Isolation, characterization, and expression in Escherichia coli of the DNA polymerase gene from Thermus aquaticus. J. Biol. Chem. 2641:6427-37.

Newell, K. J., Matrisian, L. M., Driman, D. K. (2002). Matrilysin (matrix metalloproteinase-7) expression in ulcerative colitis-related tumorigenesis. Mol. Carcinog. 34:59-63

Pitari, G., Malergue F, Martin F, Philippe J M, Massucci M T, Chabret C, Maras B, Dupre S, Naquet P, Galland (2000). Pantetheinase activity of membrane-bound Vanin-1: lack of free cysteamine in tissues of Vanin-1 deficient mice. FEBS Lett. 483:149-54.

Saiki, R. K., Scharf S, Faloona F, Mullis K B, Horn G T, Erlich H A, Arnheim N (1985) Enzymatic amplification of beta-globin genomic sequences and restriction site analysis for diagnosis of sickle cell anemia. 1985. Biotechnology. 1992; 24:476-80

Sambrook, J., Russell D W, Sambrook J (1989). Molecular cloning, Cold Spring Harbor Press, Cold Spring Harbor, N.Y.

Sharkey, D. J., Scalice E R, Christy K G Jr, Atwood S M, Daiss J L (1994). Antibodies as thermolabile switches: high temperature triggering for the polymerase chain reaction. Biotechnology (N Y). 12:506-9

Spandau, U. H, Toksoy A, Verhaart S, Gillitzer R, Kruse F E. High expression of chemokines Gro-alpha (CXCL-1), IL-8 (CXCL-8), and MCP-1 (CCL-2) in inflamed human corneas in vivo. Arch Opthalmol. 2003 June; 121(6):825-31.

von Stein, O. D., Isolation of differentially expressed genes through subtractive on hybridization. Methods Mol Biol 2001; 175:263-78

Woessner, J. F. Jr., Regulation of matrilysin in the rat uterus. Biochem Cell Biol. 1996; 74(6):777-84

The invention claimed is:

1. A method for the differentiation between ulcerative colitis and Crohn's disease based on the analysis of gene expression level profiles in biopsy samples obtained from inflamed colon tissue of a human patient, comprising determining expression levels of at least two marker genes in a biopsy sample from inflamed colon tissue from the patient, wherein said at least two marker genes are SEQ ID NO: 1 and SEQ ID NO: 2, and wherein expression of SEQ ID NO: 1 in inflamed colon tissue and lack of expression of SEQ ID NO: 2 in inflamed colon tissue is indicative of ulcerative colitis.

2. The method according to claim 1, further comprising determining the expression levels of SEQ ID NO: 1 and SEQ ID NO: 2 in a biopsy sample from non-inflamed colon tissue from the patient, wherein expression of SEQ ID NO: 1 in inflamed colon tissue and a lack of expression of SEQ ID NO: 1 in non-inflamed colon tissue, together with a lack of expression of SEQ ID NO: 2 in inflamed colon tissue and expression of SEQ ID NO: 2 in non-inflamed colon tissue, is indicative of ulcerative colitis.

3. The method according to claim 1, wherein the expression of each marker gene is determined through nucleic acid amplification of said genes using gene specific primers, and determination of the amplification results.

4. The method according to claim 3, wherein the nucleic acid amplification is performed using PCR and the gene specific primers are SEQ ID NOS: 13, 14, 15 and 16.

5. The method according to claim 3, wherein the determination of the amplification results is performed using ethidium bromide staining and visualisation under UV light.

6. The method according to claim 2, wherein the expression level of each marker gene is determined through nucleic acid amplification of said genes using gene specific primers and determination of the amplification results.

7. The method according to claim 1, further comprising determining the expression level of SEQ ID NO: 3 in the inflamed colon tissue, wherein expression of SEQ ID NO: 3 in inflamed tissue is indicative of ulcerative colitis.

8. The method according to claim 7, wherein the expression level of each marker gene is determined through nucleic acid amplification of said genes using gene specific primers, and determination of the amplification results.

9. The method according to claim 1, further comprising determining the expression level of SEQ ID NO: 4 in the inflamed colon tissue, wherein expression of SEQ ID NO: 4 in inflamed tissue is indicative of ulcerative colitis.

10. The method according to claim 9, wherein the expression level of each marker gene is determined through nucleic acid amplification of said genes using gene specific primers, and determination of the amplification results.

11. The method according to claim 1, further comprising determining the expression level of SEQ ID NOS: 3, 4, 5, 6, and 7 in the inflamed colon tissue, wherein expression of SEQ ID NOS: 3, 4, 5, 6, and 7 in the inflamed tissue is indicative of ulcerative colitis.

12. The method according to claim 11, wherein the expression level of each marker gene is determined through nucleic acid amplification of said genes using gene specific primers, and determination of the amplification results.

13. The method according to claim 12, wherein the nucleic acid amplification is performed using PCR and the gene specific primers are SEQ ID NOS: 13-26.

* * * * *